United States Patent
Saint-Jalmes et al.

(10) Patent No.: US 6,388,126 B1
(45) Date of Patent: May 14, 2002

(54) ORGANIC BASE HYDROGENOFLUOROSULPHONATES, THEIR USE IN RELEASING ORGANIC BASES FROM THEIR FLUOROHYDRATE, METHOD OF PREPARATION THEREOF, COMPOUND CONTAINING THEM

(75) Inventors: Laurent Saint-Jalmes, Meyzieu; Marcel Morel, Brignais, both of (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/768,604

(22) Filed: Jan. 25, 2001

Related U.S. Application Data

(63) Continuation of application No. 09/171,990, filed as application No. PCT/FR97/00766 on Apr. 30, 1997, now Pat. No. 6,201,149.

(30) Foreign Application Priority Data

Apr. 30, 1996 (FR) .............................. 96/05573

(51) Int. Cl.⁷ ............................ C07C 303/00
(52) U.S. Cl. .......................... 562/114; 558/44
(58) Field of Search .............................. 562/114; 558/44

(56) References Cited

U.S. PATENT DOCUMENTS 3,875,292 A * 4/1975 Wiesboeck et al.
4,131,449 A   12/1978 Entwistle
4,481,370 A   11/1984 Lin et al.

FOREIGN PATENT DOCUMENTS

| DE | 27 19 577 | 11/1977 |
| EP | 0 121 466 | 10/1984 |
| GB | 2 138 810 | 10/1984 |

OTHER PUBLICATIONS

Czarnowski, et al Z. Phys Chem. (1968) 57(3–6) 249–64.*
King, J.F et al. Tetrahedron Lett (1979)(38), 3615–18.*
Neidlein, R et al, Chem–Ztg (1980), 104(6) 200–2.*
Chemical Abstracts, vol. 93, No. 17, Oct. 27, 1980, Columbus, Ohio, Abstract No. 167055, Zibarev, A.V. et al, "Study of the behavior of pentafluorobenzoyliminosulifinyl dihalides in strong acids", XP002037177.
J. Med. Chem. (1979), 22(3), 237–47, XP002037176, Rokach, Joshua et al, Cyclic amidine inhibitors of indolamine N–methyltransferase.

* cited by examiner

*Primary Examiner*—Paul J. Killos
(74) *Attorney, Agent, or Firm*—Burns, Doane, Swecker & Mathis, L.L.P.

(57) ABSTRACT

The invention features the use of flourosulphonates to release the organic bases from their fluorohydrate. This use is characterised in that a hydrogenofluorosulphonate of an organic base is formed and in that the hydrofuoric acid which is associated with the said base or with one of its precursors is separated therefrom. The invention is useful in organic synthesis applications.

7 Claims, No Drawings

ORGANIC BASE HYDROGENOFLUOROSULPHONATES, THEIR USE IN RELEASING ORGANIC BASES FROM THEIR FLUOROHYDRATE, METHOD OF PREPARATION THEREOF, COMPOUND CONTAINING THEM

This application is a continuation, of application Ser. No. 09/171,990, filed Jan. 19, 1999 now U.S. Pat. No. 6,201,149, which is a filing under 35 U.S.C. §371 of International Application No. PCT/FR97/00766 filed on Apr. 30, 1997.

The present invention relates to the use of fluorosulphonates to release organic bases from their hydrofluoride, to hydrogen fluorosulphonates of an organic base, to processes for the preparation of fluorosulphonate(s) and to compositions of organic base fluorosulphonate(s) and of hydrofluoric acid. The invention relates more particularly to a technique for separating hydrofluoric acid from organic bases capable of forming combinations, usually constituting defined compounds, with several, at least three, molecules of unitary hydrofluoric acid (i.e. HF).

The process according to the present invention is particularly suitable for bases which constitute, with hydrofluoric acid, combinations containing more than two, advantageously three, hydrofluoric acid units.

It is well known to those skilled in the art that organic bases form, with hydrofluoric acid, complexes containing at least three hydrofluoric acid units. Generally, the weaker and softer the bases, the greater the number of hydrofluoric acid units per basic function.

Now, on account of their specific properties, fluoro compounds are in ever-increasing demand and used in applications such as agriculture and health.

Fluoro derivatives are often difficult to synthesize and often involve exchanges of various substituents with fluorine. Now, the reagent most commonly used and the cheapest for carrying out the exchange is undeniably hydrofluoric acid.

In addition, this acid is increasingly being used as a reaction medium. Certain precursors of organic bases present problems of stability, thus, carbamoyl fluorides show thermal instability which leads to the formation of isocyanate or to the formation of fluorophosgene (Hoechst, EP 639,556) which is very difficult to handle on account of its toxicity. Moreover, fluorophosgene leads to the loss of two fluorine atoms.

Accordingly, one of the aims of the present invention is to provide a form of organic bases whose use allows appreciable recovery of the hydrofluoric acid.

Another aim of the present invention is to provide a form of the above type whose use allows the hydrolysis of carbamoyl fluorides without releasing phosgenes and in particular fluorophosgenes.

Another aim of the present invention is to provide a process for preparing a form of the above type.

Another aim of the present invention is to provide a process for preparing a form of the above type which allows the release of the base from carbamoyl.

Another aim of the present invention is to provide a composition containing the said organic base and at least two equivalents of hydrofluoric acid per basic function, from which composition recovery of the hydrofluoric acid is easy.

These aims and others which will emerge later are achieved by means of using the hydrogen fluorosulphonate form of an organic base in order to separate it from the hydrofluoric acid which is combined with the said base or which is combined with one of its precursors.

Thus, in the course of the study which led to, the present invention, it has been shown that fluorosulphonic acid ($HFSO_3$) is capable of displacing complexes between organic bases and hydrofluoric acid, thus allowing the hydrofluoric acid to be recovered.

The present invention is especially of interest for certain bases, in particular phosphorus bases and especially nitrogen bases.

Thus, when the said base is a nitrogen base, it is advantageously chosen from amines (including cyclic amines) and imines (including aromatic heterocycles).

When the said base is a phosphorus base, it is advantageously chosen from phosphines (including cyclic phosphines), and aromatic heterocycles containing a phosphorus as hetero atom.

The greater the capacity of the said organic base to combine with hydrofluoric acid and the greater the number of hydrofluoric acid units with which it can combine, the greater the advantage of the present invention.

Thus, it is advantageous for the said organic base to be chosen from those whose pKa in combined form is not more than 8, advantageously not more than 7.

The said base is chosen from those capable of forming complexes with hydrofluoric acid in which the ratio between the hydrofluoric acid and the basic function (or at least one of the basic functions when is the molecule treated contains several basic functions) is at least equal to 5.

As has been outlined above, the said base is combined with hydrofluoric acid in the form of one of its precursors.

According to one particularly advantageous embodiment of the present invention, the said precursor is a precursor which releases the said base by consuming a molecule of water. This characteristic has an advantage during the in-situ preparation of the fluorosulphonate anion, as will be seen later.

According to an advantageous variant of the present invention, in the said precursor, the function which will be converted into a basic function is a function which releases a gas such as, for example, carbon dioxide.

When the said base is an amine (including an aniline), a good example of a function which releases a gas (carbon dioxide) can be found in carbamic acid derivatives, such as urea, carbamoyl [often in the form of halide, usually fluoride] or carbamate functions. These functions are derived from isocyanate functions.

Given its cost, its relative instability and its corrosiveness, it is advantageous for the said hydrogen fluorosulphonate to be formed in situ.

Accordingly, one of the aims of the present invention is to provide a process which makes it possible to release a base from one of its complexes with hydrofluoric acid.

This aim and others which will become apparent later are achieved by means of a process which includes a step a) in which the hydrogen fluorosulphonate of the said organic base is formed.

Advantageously, this process includes, after step a), a step b) in which the hydrofluoric acid is recovered from the composition thus modified.

It is possible to form the hydrogen fluorosulphonate by a simple action of fluorosulphonic acid on the complex between the hydrofluoric acid and the said organic base. This is undoubtedly a satisfactory route when an inexpensive source of such an acid is available on site.

However, it is advantageous, and this is another aim of the present invention, to be able to prepare fluorosulphonate in situ, in particular from a composition containing hydrofluoric acid, optionally combined with an organic base.

Thus, in the course of the study which led to the present invention, it has been shown that fluorosulphonic acid can readily be manufactured in situ by the action of sulphuric acid or sulphur trioxide (sulphuric anhydride or $SO_3$) on more or less anhydrous organic compositions containing hydrofluoric acid.

When the said composition is wet and/or contains no dehydrating agent, it is then advisable to use sulphur trioxide, $SO_3$, in its native form or in the form of oleum.

If the said composition contains a dehydrating agent, it may then be advantageous to use sulphuric acid, optionally containing a small amount of water (sulphuric acid at a concentration at least equal to 80%, advantageously to 90%, often to 95%). Thus, in this embodiment of the present invention, the fluorosulphonic acid is manufactured in situ by the action of sulphuric acid on the hydrofluoric acid from the composition in the presence of a dehydrating agent.

Advantageously, the said dehydrating agent is a precursor of the said base.

The said organic base is an amine and the said precursor of the said base is an isocyanate function or a function which is derived therefrom (for example carbamoyl urea [halide, usually fluoride] or carbamate).

The reaction for the synthesis of the fluorosulphonic anion is carried out at a temperature of between 0° C. and 100° C., distillation temperature of HF, advantageously between 0° C. and 50° C., preferably between 0° C. and 20° C.

Although it is possible to envisage carrying out the said recovery of the hydrofluoric acid in a different manner, and in particular by liquid extraction, it is generally preferred for step b) of hydrofluoric acid recovery to be a distillation.

The present process is particularly advantageous for recycling the base acid reagents which are increasingly being developed, in particular reagents consisting of aromatic heterocycle(s), and of hydrofluoric acid, for which family of reagents the compound [pyridine, 10HF] can be considered a prime example.

It can also be especially advantageous for the release of those so-called organic bases (particularly advantageous also for the corresponding fluorosulphonates) which contain at least one fluorophoric carbon or sulphur.

Advantageously, the said organic base contains at least one $sp^3$-hybridized carbon or an $SF_5$ as fluorophoric carbon or sulphur, respectively.

Advantageously, the said organic base contains at least one trivalent phosphorus or nitrogen atom as basic function, this atom, it goes without saying, containing a proton-accepting lone pair.

In order for the process to be particularly advantageous, the said base needs to be stable in very acidic and/or very dehydrating medium (medium similar to olea [also referred to by some as oleums]).

Another aim of the present invention is to provide compounds which allow the organic bases to be released from their complexes with several units of hydrofluoric acid, and in particular using compositions containing a high proportion of hydrofluoric acid—in general at least two units of hydrofluoric acid, advantageously at least 3 and preferably at least 4 units of hydrofluoric acid.

These aims and others which will become apparent later are achieved by means of the hydrogen fluorosulphonate of an organic base; it is desirable for the said organic base, including the combined acid, to have at least one basic function whose pKa is (measured or brought into aqueous phase) not more than 10, advantageously not more than 8, preferably not more than 6. It is desirable for this pKa to be positive and advantageously at least equal to 1, preferably at least equal to 2. Thus, organic bases whose pKa is between 1 and 8, preferably 2 and 6 (limits included) are preferred.

Organic bases whose hydrogen fluorosulphonate is targeted by the present invention, and which contain at least one fluorine atom, advantageously at least two fluorine atoms, are of special industrial interest. This or at least one of these fluorines is advantageously borne by an atom which has no aromatic nature (i.e. by an atom which is not a member of an aromatic ring) this fluorophoric atom (i.e. fluorine-bearing atom), when it is carbon, is preferably $sp^3$-hybridized; besides the fluorine atom which gives this fluorophoric atom its title, the latter atom advantageously bears one or two (identical or different) halogen atoms [preferably chosen from light halogens, i.e. chlorine or fluorine].

In other words, the said organic base whose hydrogen fluorosulphonate is targeted by the present invention, advantageously contains at least one, preferably at least two, fluorine atoms. It is also preferable for it to contain at least one fluorine on an $sp^3$-hybridized carbon, which advantageously bears one or two (identical or different) halogen atoms [preferably chosen from light halogens, i.e. chlorine or fluorine]. It is thus desirable for the organic base, whose hydrogen fluorosulphonate is targeted by the present invention, to contain as fluorophoric atom at least one carbon or at least one chalcogen from an atomic row at least equal to that of sulphur; organic bases which contain as fluorophoric atom(s) at least one $sp^3$-hybridized carbon or a hexavalent chalcogen (which, of course, cannot be oxygen), preferably sulphur (for example $SF_5$), are more particularly targeted.

Advantageously, the said fluorophoric atom (for example $sp^3$-hybridized carbon or hexavalent sulphur) bears at least two fluorine atoms.

The said organic base advantageously contains, as atom bearing the (or one of the) basic function(s) (i.e. proton accepter), a nitrogen or a trivalent phosphorus.

Among the advantageous bases, mention may be made of aromatic heterocycles such as pyridines, including quinolines, which are optionally substituted, including substitution with halogens (chlorine, fluorine, bromine, etc.) and optionally bearing, indirectly or, more advantageously, directly, at least one fluorophoric atom as defined above.

These bases advantageously correspond to the following formula:

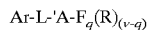

with Ar representing a base of aromatic nature in which the hetero atom bearing the (or one of the) basic function(s) (i.e. proton accepter) is either endocyclic (as in the case of pyridine or quinoline) or exocyclic (as in anilines);

with L representing a bond between Ar and 'A; with 'A representing the fluorophoric atom as defined above;

q represents the number of fluorine atoms borne by the said fluorophoric atom and is at least equal to one and not more than v;

v represents the residual valency (i.e. valency available after the bond between L and 'A has been taken into account), of the fluorophoric atom;

the groups R, which may be identical or different, (of course when v>q) represent halogens, hydrogen atoms, a carbon-based chain or can contain one or more other fluorophoric atoms.

R can attach to a position of Ar to form a ring (this ring advantageously being 4- to 8-membered, preferably 5- to 7-membered); in this case, R can advantageously take the values of L and in particular can simply be a chalcogen (in particular oxygen or sulphur) or a single bond.

L is advantageously chosen from a single bond, a chalcogen atom and a divalent carbon-based radical which can contain one or more fluorophoric atoms. In the case of a divalent carbon-based radical, the bond between L and Ar can be an $sp^2$ carbon-chalcogen bond; moreover, it may be advantageous for the bond between L and the fluorophoric atom to be a chalcogen-fluorophoric atom bond.

Ar can optionally be substituted on its available ring members, including substitution with halogens (chlorine, fluorine, bromine, etc.) and/or with other substituents corresponding to the formula:

-L'-AF$_q$(R)$_{(\nu-q)}$ detailed above:

thus, Ar represents a base of aromatic nature in which the hetero atom bearing the (or one of the) basic function(s) (i.e. a proton accepter) is either endocyclic (as in the case of pyridine or quinoline) or exocyclic (as in anilines).

Ar advantageously contains not more than about 40 carbon atoms, preferably not more than about 30, each R advantageously containing not more than about 10 carbon atoms, preferably not more than 8. L advantageously contains not more than about 10 carbon atoms, preferably not more than 8.

The total number of carbon atoms in the base is advantageously not more than about 50 carbon atoms, preferably not more than 30 carbon atoms.

Mention should be made of a base sub-family in which 'A-F$_q$(R)$_{(\nu-q)}$ represents a perfluoro radical (i.e. Rf=C$_n$F$_{2n+1}$).

Mention should be made of a base sub-family in which L represents a single bond or a chalcogen atom.

The intersection between these two sub-families is particularly advantageous.

The present invention thus relates to a composition containing both hydrofluoric acid and a hydrogen sulphonate, in which composition the molar ratio between the hydrofluoric acid and the basic functions of the said organic base (HF/basic functions of the said organic base) is at least equal to 2, advantageously equal to 3, preferably equal to 4.

The water content in the said composition is advantageously such that the number of molecules of water in the composition is not more than half (advantageously a quarter, preferably a tenth) of the number (expressed as equivalents) of basic functions present in the composition.

In addition, the composition can also contain sulphuric acid.

Needless to say, it can also contain any product used in the previous steps of the synthesis of the said organic base.

The non-limiting examples which follow illustrate the invention.

General Conditions and General Procedure

The crude reaction products were analysed by gas chromatography.

Principle

As indicated in the above description, it is economically important and was technically conceivable to recover the excess HF used to fluorinate the last but one precursor of the pTFMA by distillation after the step of lysis of the carbamoyl fluoride into pTFMA hydrofluoride:

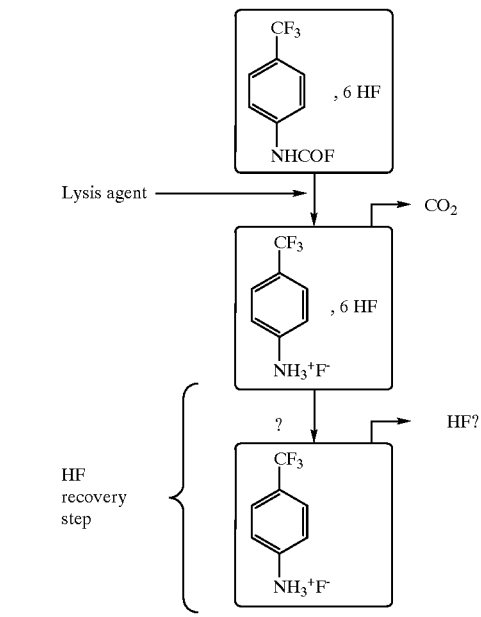

After unsuccessfully attempting to recover the "free" HF by distilling the pTFMA hydrofluoride/HF mixture, the lysis technique was tested according to a particularly advantageous embodiment of the present invention, by addition of 98% sulphuric acid to the PTFMA hydrofluoride/HF mixture.

EXAMPLE 1 (COMARATIVE)

Distillation of Hp Using a pTFMA Hydrofluoride/HF Mixture

The assay for this sample (neutralization, pTFMA assay by HPLC, assay of the fluorides by ion chromatography) gives the following proportions:

pTFMA/HF=59/41 i.e. 5.6 equivalents of HF relative to the pTFMA.

Distillation Procedure

Experimentally, the pTFMA hydrofluoride/HF mixture was heated in a 500 ml Teflon PFA reactor under a stream of nitrogen. The HF distilled off was trapped out in bubblers with potassium hydroxide, the fluorides being assayed by ion chromatography.

The distillation vessel was heated until an HF distillation plateau was reached without degradation of the trifluoromethylaniline.

The results are collated below:

| Test No. | Initial pTFMA hydrofluoride HF | T° | Duration | HF distilled off | pTFMA* found |
|---|---|---|---|---|---|
| a | pTFMA: 0.198 mol<br>HF$_{free}$: 0.911 mol | 60° C. | 1 h 30 | 0.078 mol, i.e. 8.5% of the initial "free" HF | 96% |

-continued

| Test No. | Initial pTFMA hydrofluoride HF | T° | Duration | HF distilled off | pTFMA* found |
|---|---|---|---|---|---|
| b | crude product from a) | 90°C. | 1 h 00 | 0.162 mol, i.e. 19.5% of the remaining "free" HF | 100% |
| Total | | | | 26% of the initial "free" HF | 98% |

*assay by HPLC after neutralization.

It appears that heating the pTFMA hydrofluoride/HF mixture allows only 26% of the "free" HF (HF not in hydrofluoride form) initially present to be distilled off.

The remaining HF associated with the pTFMA would appear to correspond to a complex of approximate formula:

pTFMA.4HF

These HF-base complexes are known to be difficult to decompose by simple heating.

In conclusion, heating of the pTFMA hydrofluoride/HF crude reaction product does not allow all of the HF initially present to be recycled.

EXAMPLE 2

Tests of Recovery of HF from Carbamoyl Fluoride.6HF

It was possible to observe that simple addition of 98% sulphuric acid to carbamoyl fluoride led to a considerable and immediate evolution of gas.

Infrared analysis of the gas formed demonstrates that it is essentially carbon dioxide. It appeared that the result of the above case was found. However, analyses on the crude reaction product and further studies made it possible to explain the formation of $CO_2$ by reaction between carbamoyl fluoride and $H_2SO_4$: the sulphuric acid (even at 100%) reacts with it to form pTFMA fluorosulphonate and $CO_2$.

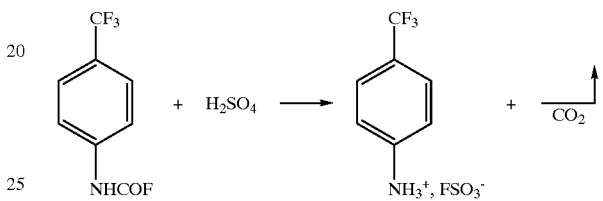

TABLE II

Treatment of the pTFMA.nHF mixture with $H_2SO_4$

| Starting mixture  ; HF | $H_2SO_4$: quality and No. of equiv. relative to the pTFMA | T°, duration | HF evolved | pTFMARY | HF not distilled off |
|---|---|---|---|---|---|
| pTFMA; HF: 0.098 mol; HF: 0.629 mol i.e. 5.4 equiv. | 100% $H_2SO_4$ 2.1 equiv. | 60° C., 2 h 90° C., 1 h | 0.517 mol, i.e. 5.3 equiv. | 98% | 1.1 equiv. of HF % i.e. = 0.1 equiv. of free HF |
| pTFMA; HF: 0.097 mol; HF: 0.709 mol i.e. 6.3 equiv. | 98% $H_2SO_4$ 2.08 equiv. | 60–65° C., 2 h 90° C., 1 h | 0.65 mol, i.e. 6.7 equiv. | 97% | HF: 1.16 equiv., i.e. 0.16 equiv. free HF |
| pTFMA; HF: 0.098 mol; HF: 0.715 mol i.e. 6.3 equiv. | 98% $H_2SO_4$ 4 equiv. | 65° C., 2 h 90° C., 1 h | 0.537 mol, i.e. 5.48 equiv. | 96.5% | HF: 1.85 equiv., i.e. 0.85 equiv. of free HF |
| pTFMA; HF: 6.6 equiv. HF | 98% $H_2SO_4$ a) 1.13 equiv. <u>3</u> | 60–65° C., 1 h 30 | | | HF: 1.47 equiv., i.e. 0.47 equiv. free HF |
| | b) additional 1 equiv. | 90° C., 1 h | | 98% | HF: 1 equiv., i.e. 0 equiv. free HF |

To the Applicant's knowledge, this water-free "lysis" of a carbamoyl halide function with sulphuric acid has never been described in the literature.

A 6-centre mechanism can be put forward to explain this reaction, the $CF_3$ group strongly activating the carbamoyl fluoride function:

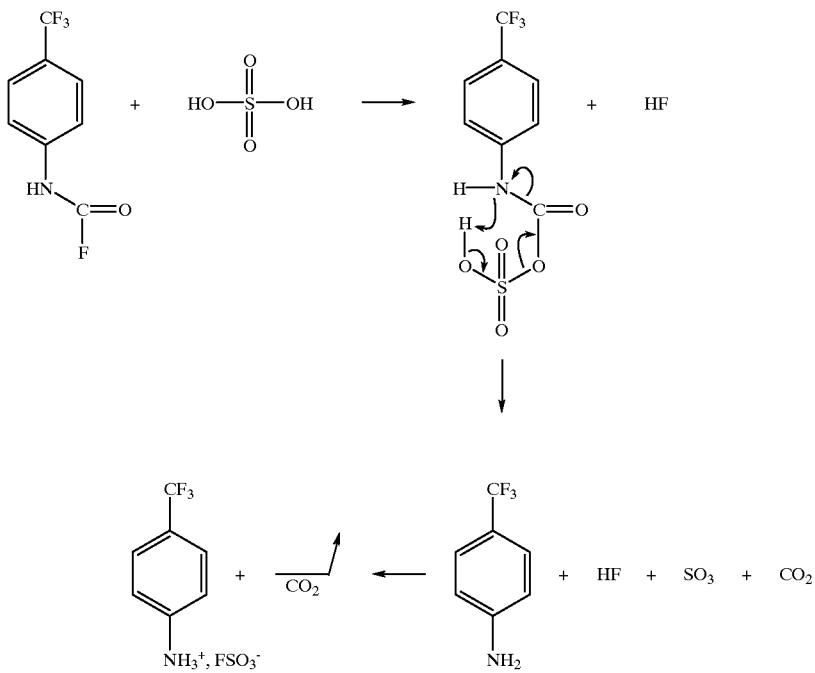

The pTFMA fluorosulphonate, characterized by $^{19}F$ NMR and IR was also synthesized by the action of fluorosulphonic acid $HFSO_3$ on pTFMA.

pTFMA fluorosulphonate is a solid which is rapidly hydrolysed by atmospheric moisture into pTFMA

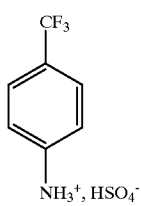

Experimentally, the tests summarized in Table II were carried out in the following way:

98 or 100% sulphuric acid was added to the above solutions at 20° C., leading to an immediate evolution of $CO_2$.

After adding the $H_2SO_4$, the homogeneous reaction mixture was heated, under a stream of nitrogen, to remove the HF, which was trapped out in bubblers containing potassium hydroxide. The fluorides obtained were assayed by ion chromatography.

After cooling to room temperature, the reaction media were analysed. After anhydrous neutralization with pentylamine, the pTFMA was assayed by HPLC.

From the results obtained, the following conclusions can thus be drawn:

The action of about 2 equivalents of $H_2SO_4$ (98 or 100%) on a mixture, HF (5 to 6 equivalents of HF relative to the carbamoyl fluoride), followed by heating to 90° C. allows virtually all of the initial "free" HF to be removed.

After removal of the HF, the medium obtained is homogeneous and liquid, and corresponds to a solution of PTFMA fluorosulphonate in $H_2SO_4$ containing a small amount of HF (0.1 to 0.2 equivalent of initial "free" HF).

The use of 4 equivalents of 98% $H_2SO_4$ limits the number of equivalents of HF distilled off. This can be explained by the water provided by the 98% $H_2SO_4$, which can hydrolyse the carbamoyl fluoride into pTFMA hydrofluoride. In this case, HF-base complexes can be formed between the base and the HF and limit the distillation of the HF, as has already been observed.

This type of HF-base complex should not be formed between pTFMA fluorosulphonate and HF.

After neutralization of the crude reaction product which has been degassed in respect of HF, the pTFMA was obtained in a yield of about 97–98% (HPLC assay).

In conclusion, the addition of 2 equivalents of 98 or 100% $H_2SO_4$ to the crude product from the fluorination of pTCMI 2 makes it possible, by heating, to recycle virtually all of the free HF initially present and to obtain a homogeneous liquid solution of pTFMA fluorosulphonate 7 in about 1 equivalent of $H_2SO_4$.

Using the solution of pTFMA fluorosulphonate in sulphuric acid after distillation of the HF, the pTFMA can be obtained by neutralization with aqueous sodium hydroxide and extraction with methylene chloride. The yield for this neutralization and extraction step is greater than 98%.

What is claimed is:

1. Hydrogen fluorosulphonate of an organic base, wherein said organic base comprises at least one fluorophoric atom chosen from $sp^3$-hybridized carbons and chalcogens from a row at least equal to that of sulphur.

2. Hydrogen fluorosulphonate according to claim 1, wherein said organic base contains at least one fluorophoric carbon or sulphur.

3. Hydrogen fluorosulphonate according to claim 1, wherein said organic base contains at least one $sp^3$-hybridized carbon or an $SF_5$.

4. Hydrogen fluorosulphonate according to claim 1, wherein said organic base contains, as a basic function, a nitrogen or a trivalent phosphorus.

5. Composition containing both hydrofluoric acid and a hydrogen sulphonate according to claim 1, wherein the molar ratio between the hydrofluoric acid and the basic functions of said organic base (HF/basic functions of said organic base) is at least equal to 2.

6. Composition according to claim 5, wherein the water content in said composition is such that the number of molecules of water in the composition is not more than half of the number of basic functions present in the composition.

7. Composition according to claim 5, wherein the composition also contains sulphuric acid and the number of molecules of water on the composition is not more than a quarter, of the number of basic functions present in the composition.

* * * * *